United States Patent
Sarangapani et al.

(10) Patent No.: US 11,931,104 B2
(45) Date of Patent: Mar. 19, 2024

(54) VISION QUALITY ASSESSMENT BASED ON MACHINE LEARNING MODEL AND WAVEFRONT ANALYSIS

(71) Applicant: Alcon Inc., Fribourg (CH)

(72) Inventors: Ramesh Sarangapani, Coppell, TX (US); Mark VonTress, Arlington, TX (US)

(73) Assignee: Alcon Inc., Fribourg (CH)

( * ) Notice: Subject to any disclaimer, the term of this patent is extended or adjusted under 35 U.S.C. 154(b) by 659 days.

(21) Appl. No.: 17/127,693

(22) Filed: Dec. 18, 2020

(65) Prior Publication Data

US 2021/0186323 A1    Jun. 24, 2021

Related U.S. Application Data

(60) Provisional application No. 62/950,425, filed on Dec. 19, 2019.

(51) Int. Cl.
*A61B 3/10* (2006.01)
*A61B 3/00* (2006.01)
(Continued)

(52) U.S. Cl.
CPC .......... *A61B 3/1015* (2013.01); *A61B 3/0025* (2013.01); *A61B 3/0033* (2013.01); *G06N 3/08* (2013.01)

(58) Field of Classification Search
CPC ......... A61B 3/02; A61B 3/102; A61B 3/1025; A61B 3/024; A61B 3/032
(Continued)

(56) References Cited

U.S. PATENT DOCUMENTS

2005/0200809 A1 * 9/2005 Dreher ............. B29D 11/00528
351/205
2007/0203478 A1 * 8/2007 Herekar .................. A61F 9/008
606/4
(Continued)

FOREIGN PATENT DOCUMENTS

| AU | 2003225909 B2 * | 5/2008 | ........... A61B 3/0025 |
| CN | 106873152 A * | 6/2017 | ......... G02B 27/0012 |
| CN | 110207835 A * | 9/2019 | |

OTHER PUBLICATIONS

Alexander Leube, et al., Machine learning based predictions of subjective refractive errors of the human eye, Proceedings of the 12th international joint conference on biomedical engineering systems and technologies [online], Feb. 24, 2019, pp. 199-205, vol. 5.

(Continued)

*Primary Examiner* — Dawayne Pinkney

(57) ABSTRACT

A system and method of assessing vision quality of an eye is presented, with a controller having a processor and tangible, non-transitory memory on which instructions are recorded. The controller is configured to selectively execute at least one machine learning model. Execution of the instructions by the processor causes the controller to: receive wavefront aberration data of the eye and express the wavefront aberration data as a collection of Zernike polynomials. The controller is configured to obtain a plurality of input factors based on the collection of Zernike polynomials. The plurality of input factors is fed into the at least one machine learning model, which is trained to analyze the plurality of input factors. The machine learning model generates at least one vision correction factor based in part on the plurality of input factors.

7 Claims, 3 Drawing Sheets

(51) Int. Cl.
 *A61B 3/02* (2006.01)
 *G06N 3/08* (2023.01)
(58) Field of Classification Search
 USPC ....... 351/205, 200, 206, 222, 223, 239, 240, 351/241, 242, 246
 See application file for complete search history.

(56) References Cited

U.S. PATENT DOCUMENTS

2018/0136486 A1* 5/2018 Macnamara ............. A61B 3/14
2019/0110753 A1* 4/2019 Zhang ................... G16H 50/20
2019/0258930 A1 8/2019 Ohlendorf et al.

OTHER PUBLICATIONS

Arne Ohlendorf, A machine learning approach to determine refractive errors of the eye, Investigative Ophthalmology & Visual Science, Jun. 1, 2017, p. 1136, vol. 58, No. 8.

* cited by examiner

VISION QUALITY ASSESSMENT BASED ON MACHINE LEARNING MODEL AND WAVEFRONT ANALYSIS

INTRODUCTION

The disclosure relates generally to a system and method of assessing vision quality of an eye, based on at least one machine learning model and wavefront analysis. Humans have five basic senses: sight, hearing, smell, taste and touch. Sight gives us the ability to visualize the world around us and connects us to our surroundings. According to some scientific reports, the brain devotes more space to processing and storing visual information than the other four senses combined, underscoring the importance of sight. Many people worldwide have issues with quality of vision, due in large part to refractive errors. Refractive errors of the eye may be generally categorized as lower-order aberrations and higher-order aberrations. Lower-order aberrations include nearsightedness, farsightedness as well as astigmatism. Higher-order aberrations include many varieties of aberrations, such as coma, trefoil and spherical aberration. Traditional eye examination procedures result in an assessment of vision quality that only assess the lower-order aberrations of the eye.

SUMMARY

Disclosed herein is a system and method of assessing vision quality of an eye, with a controller having a processor and tangible, non-transitory memory on which instructions are recorded. The controller is configured to selectively execute at least one machine learning model. Execution of the instructions by the processor causes the controller to: receive wavefront aberration data of the eye and express the wavefront aberration data as a collection of Zernike polynomials. The controller is configured to obtain a plurality of input factors based on the collection of Zernike polynomials. The plurality of input factors is fed into at least one machine learning model, which is trained to analyze the plurality of input factors. The machine learning model generates at least one vision correction factor based in part on the plurality of input factors. The vision correction factor may be programmed into a laser device for reshaping the eye during a vision correction procedure/refractive surgery. The vision correction factor may be employed for aiding in the selection of spectacles, contact lens and/or intraocular lens for the eye.

The plurality of input factors may include respective wavefront coefficients for defocus, primary spherical aberration, oblique astigmatism and vertical astigmatism. The vision correction factor may be a manifest refraction spherical equivalent. The vision correction factor may be a log MAR (logarithm of a minimum angle of resolution) uncorrected visual acuity factor. The at least one machine learning model may incorporate a neural network and/or a support vector regression model.

The machine learning model may include a first machine learning model and a second machine learning model. Training the first machine learning model may include receiving a first training dataset having respective wavefront aberration measurements and respective measured manifest refraction spherical equivalent values of a first set of patients. First training input values are obtained based upon the respective wavefront aberration measurements and applied to a respective input layer of the first machine learning model. The respective measured manifest refraction spherical equivalent values may include pre-operative data and post-operative data. The respective measured manifest refraction spherical equivalent values may be fed to a respective output layer of the first machine learning model.

The first training input values may be employed to generate a first plurality of weight values associated with respective nodes of the first machine learning model. The first set of patients in the first training dataset may be characterized by a respective health status and/or a respective biometric parameter fitting within a first predefined maximum and a first predefined minimum. The respective biometric parameter may be an anterior chamber depth, a lens thickness, lens diameter or other dimension.

Training the second machine learning model may include receiving a second training dataset having the respective wavefront aberration measurements and the respective measured manifest refraction spherical equivalent values of a second set of patients. Second training input values are obtained based upon the respective wavefront aberration measurements. The second training input values are applied to the respective input layer of the second machine learning model. The respective measured manifest refraction spherical equivalent values are fed to the respective output layer of the second machine learning model. The second training input values may be used to generate a second plurality of weight values associated with respective nodes of the second machine learning model. The second set of patients in the second training dataset may be characterized by a respective health status and/or respective biometric parameter fitting within a second predefined maximum and a second predefined minimum.

The above features and advantages and other features and advantages of the present disclosure are readily apparent from the following detailed description of the best modes for carrying out the disclosure when taken in connection with the accompanying drawings.

DETAILED DESCRIPTION

Figure 1:
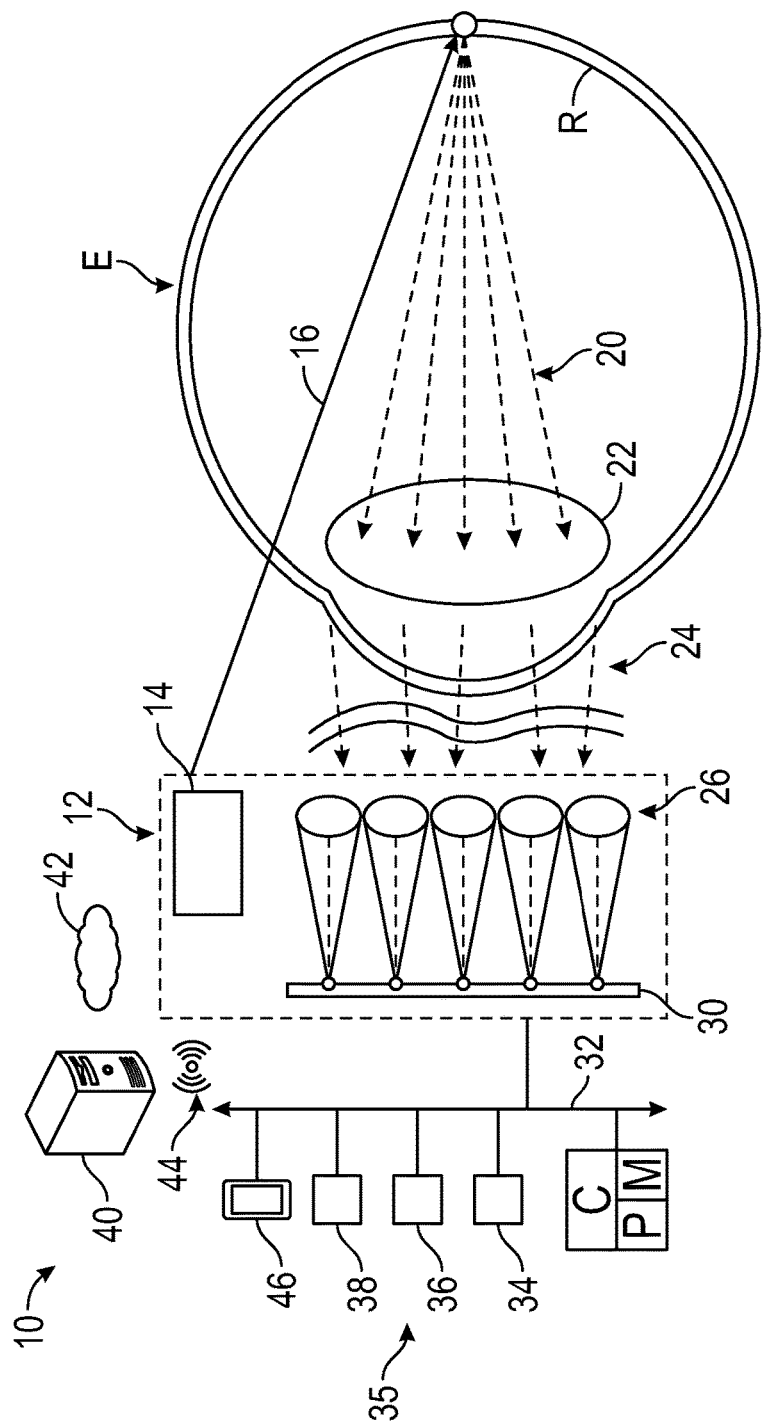
FIG. 1 is a schematic illustration of a system for assessing vision quality of an eye, the system having a controller.

Referring to the drawings, wherein like reference numbers refer to like components, FIG. 1 schematically illustrates a system 10 for assessing vision quality of an eye E.

As described below, the system 10 employs a robust approach utilizing one or more machine learning models, optimizing the assessment of vision quality and resulting in a greater success rate for prediction of vision quality. Referring to FIG. 1, the system 10 includes a refraction device 12 having a light source 14 configured to project a beam 16 of light into the eye E. The beam 16 is reflected by the retina R. Referring to FIG. 1, the reflected light 20 exits the eye E as wavefront 24, after travelling through the lens 22. The wavefront 24 is characterized by distortions unique to the physical construction of the eye E.

Referring to FIG. 1, the wavefront 24 is captured by a lenslet array 26 and detected by a sensor 30. An aberration map of the eye E is created by comparing the shape of the wavefront 24 captured with that of a pre-programmed reference wavefront having the same pupil size (as the wavefront 24 passes through the pupil in the eye E). For example, points of difference between the two may be obtained at specific points. The refraction device 12 may include associated beam guiding elements (not shown), electronic components and other components available to those skilled in the art. It is understood that the refraction device 12 may take many different forms and include multiple and/or alternate components.

Referring to FIG. 1, the system 10 includes a controller C configured to receive data from the sensor 30. The controller C may be embedded in the refraction device 12. Referring to FIG. 1, the controller C may be configured to communicate with the refraction device 12 and other entities via a short-range network 32. The short-range network 32 may be wireless or may include physical components. The short-range network 32 may be a bus implemented in various ways, such as for example, a serial communication bus in the form of a local area network. The local area network may include, but is not limited to a Controller Area Network (CAN), a Controller Area Network with Flexible Data Rate (CAN-FD), Ethernet, blue tooth, WIFI and other forms of data connection. The short-range network 32 may be a Bluetooth™ connection, defined as being a short-range radio technology (or wireless technology) aimed at simplifying communications among Internet devices and between devices and the Internet. Bluetooth™ is an open wireless technology standard for transmitting fixed and mobile electronic device data over short distances and creates personal networks operating within the 2.4 GHz band. Other types of connections may be employed.

Referring to FIG. 1, the controller C may be in communication with a user interface 34, which may include a display unit. Additionally, the controller C may be configured to communicate with a remote server 40 and/or a cloud unit 42, via a long-range network 44. The remote server 40 may be a private or public source of information maintained by an organization, such as for example, a research institute, a company, a university and/or a hospital. The cloud unit 42 may include one or more servers hosted on the Internet to store, manage, and process data. The long-range network 44 may be a Wireless Local Area Network (LAN) which links multiple devices using a wireless distribution method, a Wireless Metropolitan Area Networks (MAN) which connects several wireless LANs or a Wireless Wide Area Network (WAN) which covers large areas such as neighboring towns and cities. Other types of connections may be employed.

The controller C may be configured to receive and transmit wireless communication to the remote server 40 through a mobile application 46, shown in FIG. 1. The mobile application 46 may in communication with the controller C via the short-range network 32 such that it has access to the data in the controller C. In one example, the mobile application 46 is physically connected (e.g. wired) to the controller C. In another example, the mobile application 46 is embedded in the controller C. The circuitry and components of a remote server 40 and mobile application 46 ("apps") available to those skilled in the art may be employed.

The controller C has at least one processor P and at least one memory M (or non-transitory, tangible computer readable storage medium) on which are recorded instructions for executing a method 100. Method 100 is shown in and described below with reference to FIG. 2. The controller C is specifically programmed to selectively execute one or more machine learning models 35 ("one or more" omitted henceforth), such as first machine learning model 36 and second machine learning 38, shown in FIG. 1. The controller C may access the machine learning models 35 via the short-range network 32, the long-range network 44 and/or mobile application 46. Alternatively, the machine learning models 35 may be embedded in the controller C. The machine learning models 35 may be configured to find parameters, weights or a structure that minimizes a respective cost function and may incorporate respective regression models.

Figure 2:
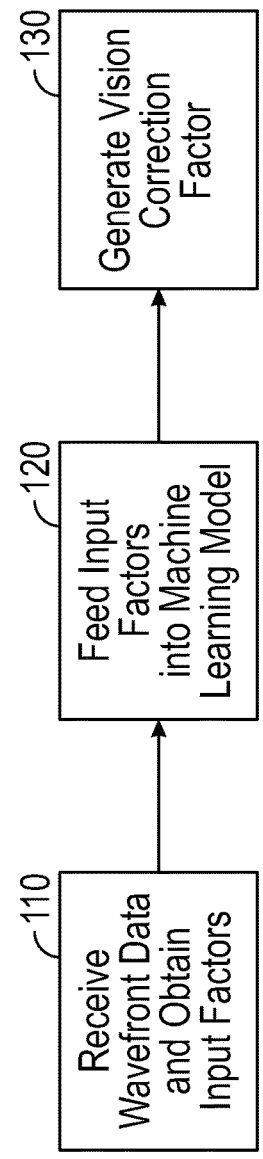
FIG. 2 is a schematic flowchart for a method executable by the controller of FIG. 1.

Referring now to FIG. 2, a flow chart of method 100 executable by the controller C of FIG. 1 is shown. Method 100 need not be applied in the specific order recited herein and some blocks may be omitted. The memory M can store controller-executable instruction sets, and the processor P can execute the controller-executable instruction sets stored in the memory M.

Per block 110 of FIG. 2, the controller C is configured to receive wave front aberration data of the eye E and translate or express it in terms of a collection of Zernike polynomials. The wavefront aberration data (A) is decomposed into a set of orthogonal polynomials on a circle such that: $A=\Sigma_{i,j} a_{i,j} Z_i^j$, where $a_{i,j}$ are respective wavefront coefficients measured on the eye E and $Z_i^j$ represents a Zernike polynomial. Each Zernike polynomial describes the type or kind of aberration existing at a specific point on the wavefront 24 after it passes through the eye E.

The controller C is configured to obtain a plurality of input factors based on the collection of Zernike polynomials, with the plurality of input factors being one or more of the respective wavefront coefficients measured on the eye E. In one example, the controller C employs two input factors: the respective wavefront coefficients for defocus ($Z_2^0$) and primary spherical aberration ($Z_4^0$). In another example, the controller C employs four input factors: respective wavefront coefficients for defocus ($Z_2^0$), primary spherical aberration ($Z_4^0$), oblique astigmatism ($Z_2^{-2}$) and vertical astigmatism ($Z_2^2$).

Per block 120 of FIG. 2, the method 100 includes feeding the plurality of input factors into the machine learning models 35, which are trained to analyze the plurality of input factors. Per block 130 of FIG. 2, the controller C is configured to generate at least one vision correction factor by executing the machine learning models 35, based in part on the plurality of input factors. The vision correction factor may include components of refraction: sphere, cylinder and spherical equivalent, and may be expressed as a manifest refraction spherical equivalent (MRSE). The vision correction factor may be expressed as a log MAR (logarithm of a minimum angle of resolution) uncorrected visual acuity factor. The vision correction factor may be employed to establish ablation profiles for refractive surgery, as well as for aiding in the selection of spectacles, contact lens and/or intraocular lens for the eye. Additionally, the controller C may be configured to create a patient profile for the patient (with the eye E) in the cloud 42 and/or remote server 40, via the long-range network 44, and upload or "save" the vision correction factor into the patient profile.

Figure 3:
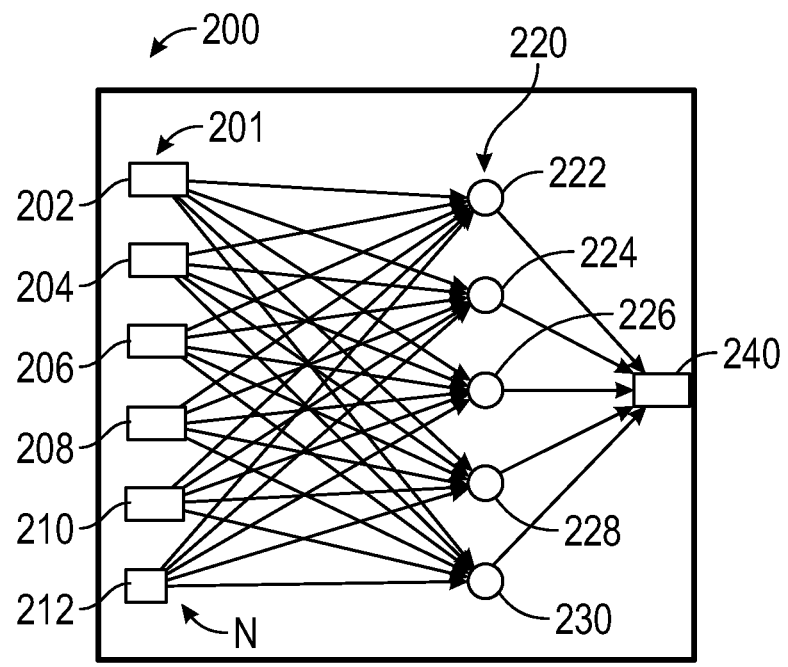
FIG. 3 is a schematic example of a neural network executable by the controller of FIG. 1.

The machine learning models 35 of FIG. 1 may include a neural network, an example of which is shown in FIG. 3. Referring to FIG. 3, the neural network 200 is a feedforward artificial neural network having at least three layers, including an input layer 201, at least one hidden layer 220 and an output layer 240. Each layer is composed of respective nodes N configured to perform an affine transformation of a linear sum of inputs. The respective nodes N are characterized by a respective bias and respective weighted links. The parameters of each respective node N may be independent of others, i.e., characterized by a unique set of weights. The input layer 201 may include first input node 202, second input node 204, third input node 206, fourth input node 208, fifth input node 210 and sixth input node 212. The respective nodes N in the input layer 201 receive the input, normalize them and forward them to respective nodes N in the hidden layer 220.

Referring to FIG. 3, the hidden layer 220 may include first hidden node 222, second hidden node 224, third hidden node 226, fourth hidden node 228 and fifth hidden node 230. Each respective node N in a subsequent layer computes a linear combination of the outputs of the previous layer. A network with three layers would form an activation function $f(x)=f(3)(f(2)(f(1)(x)))$. The activation function $f$ may be linear for the respective nodes N in the output layer 240. The activation function $f$ may be a sigmoid for the hidden layer 220. A linear combination of sigmoids may be used to approximate a continuous function characterizing the output vector y. The patterns recognized by the neural network 200 may be translated or converted into numerical form and embedded in vectors or matrices.

Figure 4:
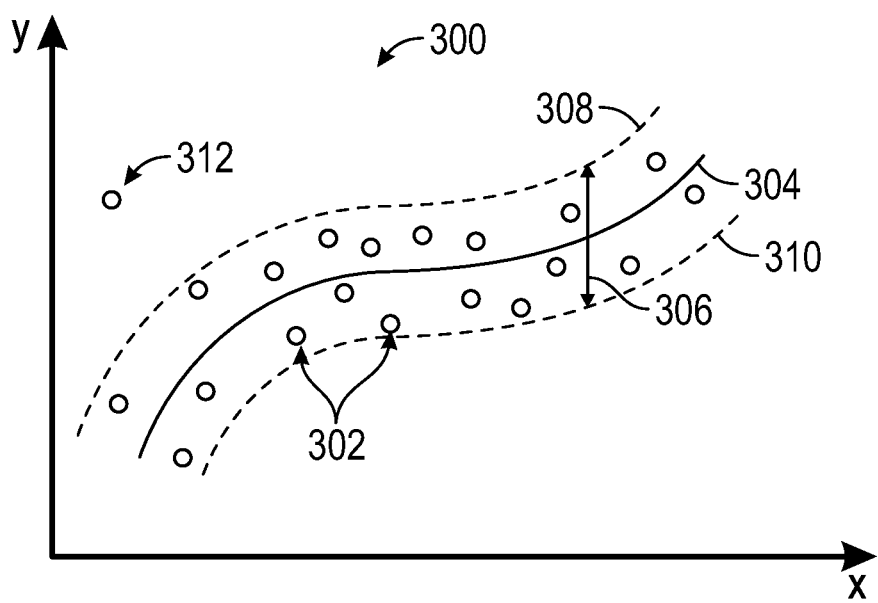
FIG. 4 is a schematic example of a support vector regression (SVR) network executable by the controller of FIG. 1.

The machine learning models 35 may include a support vector regression model 300, an example of which is shown in FIG. 4. The support vector regression model 300 is configured to find a function (hyperplane 304 in FIG. 4) such that the data points 302 are within a margin 306 from this function, i.e., inside a first boundary line 308 and a second boundary line 310. Referring to FIG. 4, the hyperplane 304 may be defined as the line that will match the input vector x to the output vector y, i.e. predict a target value. The hyperplane 304 is individualized so as to maximize the margin 306 and minimize a predefined error. If there are points (such as extraneous point 312) that are outside the margin 306, a penalty may be built into the support vector regression model 300. Prior to ascertaining the hyperplane 304, the support vector regression model 300 may employ a kernel function to map a lower dimensional dataset into a higher dimensional dataset. Other machine learning models available to those skilled in the art may be employed.

The machine learning models 35 may employ deep learning maps to match an input vector x to an output vector y by learning an activation function $f$ such that $f(x)$ maps to y. A training process enables the machine learning models 35 to correlate the appropriate activation function $f(x)$ for transforming the input vector x to the output vector y. For example, in the case of a simple linear regression model, two parameters are learned: a bias and a slope. The bias is the level of the output vector y when the input vector x is 0 and the slope is the rate of predicted increase or decrease in the output vector y for each unit increase in the input vector x. Once the machine learning models 35 are respectively trained, estimated values of the output vector y may be computed with new values of the input vector x.

Referring to FIG. 1, the controller C may be configured to obtain one or more training datasets from the remote server 40 via the long-range network 44. Training the first machine learning model 36 and second machine learning model 38 may include receiving a first training dataset and a second training dataset having respective wavefront aberration measurements and respective measured manifest refraction spherical equivalent values of a first set of patients and a second set of patients, respectively. The training datasets may be stratified based on biometric parameters of the eye. In other words, the process may be optimized by grouping the training datasets for similar-sized dimensions of eyes or other health status factors (e.g. grouping patients affected by glaucoma in the first set of patients and patients affected by a history of retinal detachment in the second set of patients).

In one non-limiting example, the first set of patients in the first training dataset may be characterized by a respective biometric parameter fitting within a first predefined maximum and a first predefined minimum. The respective biometric parameter may be an anterior chamber depth, a lens thickness, lens diameter or other physical dimension of the eye. The second set of patients in the second training dataset may be characterized by a respective biometric parameter fitting within a second predefined maximum and a second predefined minimum.

First and second training input values may be respectively obtained based upon the respective wavefront aberration measurements and applied to a respective input layer of the first machine learning model 36 and second machine learning model 38. The respective measured manifest refraction spherical equivalent values may include pre-operative data and post-operative data. The respective measured manifest refraction spherical equivalent values may be fed to a respective output layer of the first machine learning model 36 and second machine learning model 38. The first and second training input values, respectively, may be used to generate a first plurality of weight values and a second plurality of weight values associated with respective nodes of the first machine learning model 36 and second machine learning model 38. This may be done by a training program separate from the refraction device 12 and/or controller C.

Figure 5:
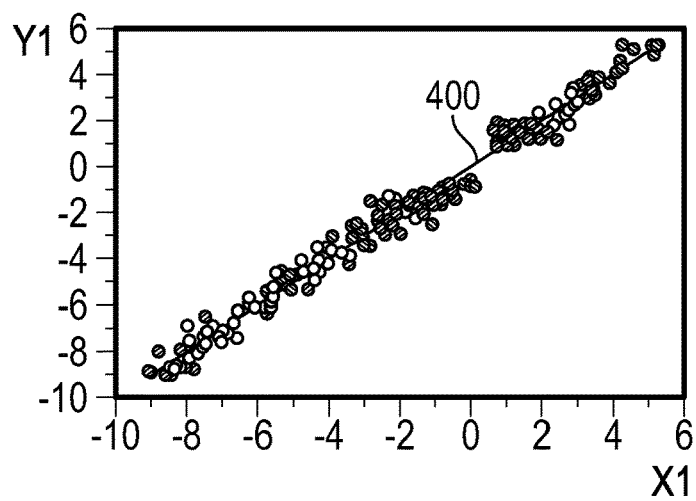
FIG. 5 is a schematic graph illustrating measured values (vertical axis) and predicted values (horizontal axis) of the manifest refraction spherical equivalent for pre-operative data.
Figure 6:
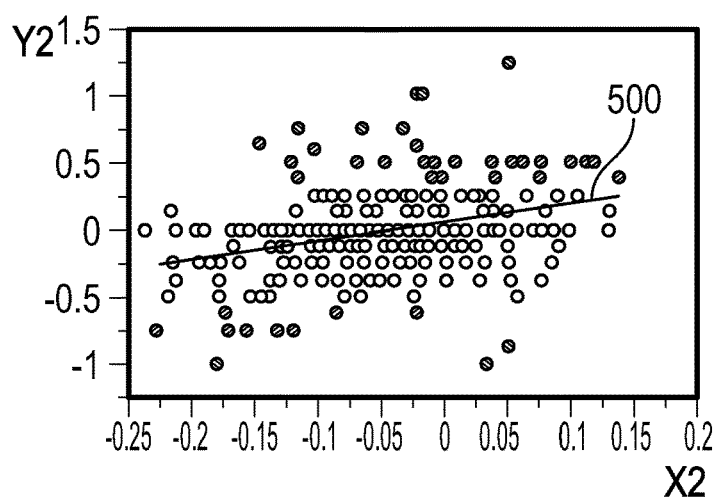
FIG. 6 is a schematic graph illustrating measured values (vertical axis) and predicted values (horizontal axis) of the manifest refraction spherical equivalent for post-operative data.
Figure 7:
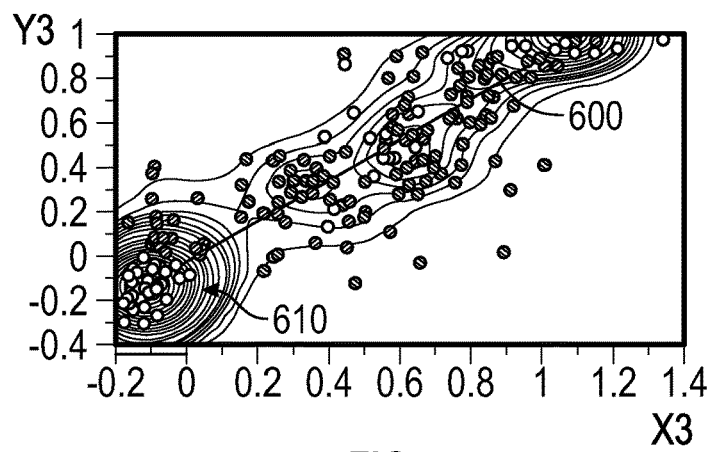
FIG. 7 is a schematic graph illustrating measured values (vertical axis) and predicted values (horizontal axis) of log MAR (logarithm of a minimum angle of resolution) uncorrected visual acuity for pre-operative and post-operative data.

Referring now to FIGS. 5, 6 and 7, schematic graphs are shown representing various examples of fitted models using a topographic guided laser refractive study. FIG. 5 shows model fit line 400 for pre-operative data, with the vertical axis Y1 indicating measured manifest refraction spherical equivalent (MRSE) values, and the horizontal axis X1 indicating predicted MRSE values. FIG. 6 shows model fit line 500 for post-operative data, with the vertical axis Y2 indicating measured MRSE values, and the horizontal axis X2 indicating predicted MRSE values. Note that the scales are different in FIGS. 5 and 6, with FIG. 6 having a smaller respective range.

FIG. 7 shows model fit line 600 and respective contours 610 for both preoperative and post-operative data, with the vertical axis Y3 indicating measured log MAR (logarithm of a minimum angle of resolution) uncorrected visual acuity values, and the horizontal axis X3 indicating predicted log MAR (logarithm of a minimum angle of resolution) uncorrected visual acuity values. Table 1 and Table 2 below show a comparison of the fitted models of FIGS. 5 and 6, respectively, with a linear sum of second order Zernike polynomials and fourth order Zernike polynomials.

TABLE 1

Pre-Operative Data

|  | Machine Learning Model Fit | $2^{nd}$ Order Zernike | $4^{th}$ Order Zernike |
|---|---|---|---|
| Mean Absolute Prediction Error | 0.314 | 0.437 | 0.531 |
| Percentage Success | 78.0 | 65.5 | 54.1 |
| Deviation Factor | 0.988 | 0.987 | 0.984 |

TABLE 2

Post-Operative Data

|  | Machine Learning Model Fit | $2^{nd}$ Order Zernike | $4^{th}$ Order Zernike |
|---|---|---|---|
| Mean Absolute Prediction Error | 0.194 | 0.378 | 0.423 |
| Percentage Success | 93.1 | 73.4 | 68.9 |
| Deviation Factor | 0.090 | 0.193 | 0.167 |

As shown by Table 1 and Table 2 above, the machine learning models 35 improve both the mean absolute prediction error and the prediction success rate for assessment of vision quality. Additionally, the system 10 eliminates the need for pupil diameter rescaling when observing objects at distance.

The controller C of FIG. 1 includes a computer-readable medium (also referred to as a processor-readable medium), including a non-transitory (e.g., tangible) medium that participates in providing data (e.g., instructions) that may be read by a computer (e.g., by a processor of a computer). Such a medium may take many forms, including, but not limited to, non-volatile media and volatile media. Non-volatile media may include, for example, optical or magnetic disks and other persistent memory. Volatile media may include, for example, dynamic random-access memory (DRAM), which may constitute a main memory. Such instructions may be transmitted by one or more transmission media, including coaxial cables, copper wire and fiber optics, including the wires that comprise a system bus coupled to a processor of a computer. Some forms of computer-readable media include, for example, a floppy disk, a flexible disk, hard disk, magnetic tape, other magnetic medium, a CD-ROM, DVD, other optical medium, punch cards, paper tape, other physical medium with patterns of holes, a RAM, a PROM, an EPROM, a FLASH-EEPROM, other memory chip or cartridge, or other medium from which a computer can read.

Look-up tables, databases, data repositories or other data stores described herein may include various kinds of mechanisms for storing, accessing, and retrieving various kinds of data, including a hierarchical database, a set of files in a file system, an application database in a proprietary format, a relational database management system (RDBMS), etc. Each such data store may be included within a computing device employing a computer operating system such as one of those mentioned above, and may be accessed via a network in one or more of a variety of manners. A file system may be accessible from a computer operating system, and may include files stored in various formats. An RDBMS may employ the Structured Query Language (SQL) in addition to a language for creating, storing, editing, and executing stored procedures, such as the PL/SQL language mentioned above.

The detailed description and the drawings or FIGS. are supportive and descriptive of the disclosure, but the scope of the disclosure is defined solely by the claims. While some of the best modes and other embodiments for carrying out the claimed disclosure have been described in detail, various alternative designs and embodiments exist for practicing the disclosure defined in the appended claims. Furthermore, the embodiments shown in the drawings or the characteristics of various embodiments mentioned in the present description are not necessarily to be understood as embodiments independent of each other. Rather, it is possible that each of the characteristics described in one of the examples of an embodiment can be combined with one or a plurality of other desired characteristics from other embodiments, resulting in other embodiments not described in words or by reference to the drawings. Accordingly, such other embodiments fall within the framework of the scope of the appended claims.

What is claimed is:

1. A system for assessing vision quality of an eye, the system comprising:

a controller having a processor and tangible, non-transitory memory on which instructions are recorded, the controller being configured to selectively execute at least one machine learning model;

wherein execution of the instructions by the processor causes the controller to:

receive wavefront aberration data of the eye and express the wavefront aberration data as a collection of Zernike polynomials;

obtain a plurality of input factors based on the collection of Zernike polynomials;

feed the plurality of input factors into the at least one machine learning model, the at least one machine learning model being trained to analyze the plurality of input factors; and generate, via the at least one machine learning model, at least one vision correction factor based in part on the plurality of input factors, wherein the at least one machine learning model includes a first machine learning model and a second machine learning model, wherein training the first machine learning model includes:

receiving a first training dataset having respective wavefront aberration measurements and respective measured manifest refraction spherical equivalent values of a first set of patients;

obtaining first training input values based upon the respective wavefront aberration measurements and applying the training input values to a respective input layer of the first machine learning model;

feeding the respective measured manifest refraction spherical equivalent values to a respective output layer of the first machine learning model; and generating a first plurality of weight values associated with respective nodes of the first machine learning model based in part on the first training input values, wherein the first set of patients in the first training dataset is characterized by an eye dimension fitting within a first predefined maximum and a first predefined minimum, and wherein training the second machine learning model includes:

receiving a second training dataset having the respective wavefront aberration measurements and the respective measured manifest refraction spherical equivalent values of a second set of patients;
obtaining second training input values based upon the respective wavefront aberration measurements and applying the second training input values to the respective input layer of the second machine learning model;
feeding the respective measured manifest refraction spherical equivalent values to the respective output layer of the second machine learning model; and
generating a second plurality of weight values associated with respective nodes of the second machine learning model based in part on the second training input values,
wherein the second set of patients in the second training dataset is characterized by an eye dimension fitting within a second predefined maximum and a first predefined minimum that is different from the first predefined maximum and a first predefined minimum.

2. The system of claim 1, wherein:
the plurality of input factors includes respective wavefront coefficients for defocus, primary spherical aberration, oblique astigmatism and vertical astigmatism.

3. The system of claim 1, wherein:
the at least one vision correction factor is a manifest refraction spherical equivalent factor.

4. The system of claim 1, wherein:
the at least one vision correction factor is a log MAR (logarithm of a minimum angle of resolution) uncorrected visual acuity factor.

5. The system of claim 1, wherein:
the at least one machine learning model incorporates a neural network.

6. The system of claim 1, wherein:
the at least one machine learning model incorporates a support vector regression model.

7. The system of claim 1, wherein:
the respective measured manifest refraction spherical equivalent values include respective pre-operative data and respective post-operative data.

* * * * *